(12) United States Patent
Pai et al.

(10) Patent No.: US 9,766,369 B2
(45) Date of Patent: *Sep. 19, 2017

(54) DETECTOR, PREAMPLIFIER SELECTION APPARATUS, SYSTEMS, AND METHODS

(71) Applicant: Halliburton Energy Services, Inc., Houston, TX (US)

(72) Inventors: Raj Pai, Houston, TX (US); Marian Morys, Downingtown, PA (US); Homi Phiroze Cooper, Houston, TX (US); John Thomas, Harleysville, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/053,616

(22) Filed: Feb. 25, 2016

(65) Prior Publication Data

US 2016/0170080 A1    Jun. 16, 2016

Related U.S. Application Data

(63) Continuation of application No. 13/583,118, filed as application No. PCT/US2010/026662 on Mar. 9, 2010, now Pat. No. 9,304,227.

(51) Int. Cl.
*G01V 8/10* (2006.01)
*E21B 47/06* (2012.01)
(Continued)

(52) U.S. Cl.
CPC .............. *G01V 8/10* (2013.01); *E21B 47/065* (2013.01); *E21B 47/123* (2013.01); *G01N 21/27* (2013.01);
(Continued)

(58) Field of Classification Search
CPC ........ G01J 3/02; G01J 3/38; G01J 3/42; G01J 5/20
See application file for complete search history.

(56) References Cited

U.S. PATENT DOCUMENTS

| | | | | |
|---|---|---|---|---|
| 4,323,309 A | * | 4/1982 | Akitomo | G01J 3/42 356/319 |
| 5,041,727 A | * | 8/1991 | Kojima | G01J 3/42 250/352 |

(Continued)

FOREIGN PATENT DOCUMENTS

| | | |
|---|---|---|
| EP | 0271602 A1 | 6/1988 |
| JP | 02221823 A | 9/1990 |

(Continued)

OTHER PUBLICATIONS

"U.S. Appl. No. 13/583,118, Final Office Action mailed Sep. 23, 2015", 14 pgs.

(Continued)

*Primary Examiner* — Casey Bryant
(74) *Attorney, Agent, or Firm* — Gilliam IP PLLC

(57) ABSTRACT

In some embodiments, apparatus and systems, as well as methods, may operate to select from multiple optical detectors and/or multiple detector amplifiers to form combinations of detectors and amplifiers as part of an optical detection system. The selection may be based on minimizing noise equivalent power (NEP) of the optical detector or a combination of an optical detector and a detector amplifier over a desired temperature range. Additional apparatus, systems, and methods are disclosed.

17 Claims, 8 Drawing Sheets

(51) Int. Cl.
*E21B 47/12* (2012.01)
*G01N 21/27* (2006.01)
*G01J 1/44* (2006.01)
*G01V 8/00* (2006.01)
*G01J 5/22* (2006.01)

(52) U.S. Cl.
CPC ......... *G01J 5/22* (2013.01); *G01J 2001/4406* (2013.01); *G01V 8/00* (2013.01)

(56) References Cited

U.S. PATENT DOCUMENTS

| | | | |
|---|---|---|---|
| 7,574,325 | B2 | 8/2009 | Dykstra |
| 2003/0016356 | A1 | 1/2003 | Adachi et al. |
| 2006/0175547 | A1* | 8/2006 | DiFoggio ............... G01J 3/02 250/269.1 |
| 2013/0119246 | A1 | 5/2013 | Pai et al. |

FOREIGN PATENT DOCUMENTS

| | | | |
|---|---|---|---|
| JP | 2221823 A | | 9/1990 |
| JP | 08184495 | | 7/1996 |
| JP | 08184495 A | * | 7/1996 |
| JP | 8184495 A | | 7/1996 |
| JP | 2002041823 | | 2/2002 |
| WO | WO-2011112185 A1 | | 9/2011 |

OTHER PUBLICATIONS

"U.S. Appl. No. 13/583,118, Non Final Office Action mailed May 4, 2015", 19 pgs.
"U.S. Appl. No. 13/583,118, Notice of Allowance mailed Dec. 2, 2015", 7 pgs.
"U.S. Appl. No. 13/583,118, Response filed Aug. 3, 2015 to Non Final Office Action mailed May 4, 2015", 11 pgs.
"U.S. Appl. No. 13/583,118, Response filed Nov. 23, 2015 to Final Office Action mailed Sep. 23, 2015", 10 pgs.
"Australian Application Serial No. 2010347761, Examination Report No. 2 mailed Oct. 9, 2013", 3 pgs.
"Australian Application Serial No. 2010347761, Examination Report No. 3 mailed Mar. 25, 2014", 3 pgs.
"Australian Application Serial No. 2010347761, Response filed Feb. 26, 2014 to Examination Report No. 2 mailed Oct. 9, 2013", 19 pgs.
"Australian Application Serial No. 201347761, Examination Report No. 1 mailed Oct. 11, 2012", 5 pgs.
"Australian Application Serial No. 201347761, Response filed May 8, 2014 to Examiner's Third Report mailed Mar. 25, 2014", 18 pgs.
"Australian Application Serial No. 201347761, Response filed Sep. 2, 2013 to Examiner's First Report mailed Oct. 11, 2012", 16 pgs.
"International Application Serial No. PCT/US10/26662 Invitation to Pay Additional Fee mailed Mar. 14, 2011", 7.
"International Application Serial No. PCT/US10/26662, International Search Report mailed Jun. 4, 2011", 9 pgs.
"International Application Serial No. PCT/US10/26662, Response filed Apr. 11, 2011 to Invitation to Pay Additional Fee mailed Mar. 14, 2011", 1 pg.
"International Application Serial No. PCT/US10/26662, Response filed Aug. 29, 2011 to Written Opinion mailed Jun. 14, 2011", 8 pgs.
"International Application Serial No. PCT/US10/26662, Written Opinion mailed Jun. 14, 2011", 12 pgs.
"International Application Serial No. PCT/US2010/026662, International Preliminary Report on Patentability mailed Aug. 29, 2012", 13 pgs.
"International Application Serial No. PCT/US2010/026662, Invitation to Restrict or Pay Additional Fees mailed Apr. 13, 2012", 4 pgs.
"International Application Serial No. PCT/US2010/026662, Response filed May 9, 2012 to Invitation to Restrict or Pay Additional Fees mailed Apr. 13, 2012", 5 pgs.
"International Application Serial No. PCT/US2010/026662, Written Opinion mailed Jun. 13, 2012", 11 pgs.
"Malaysian Application Serial No. PI2011005959, Preliminary Examination Report mailed Sep. 3, 2012", 2 pgs.
"Malaysian Application Serial No. PI2011005959, Substantive Examination Report mailed Nov. 13, 2015", 3 pgs.
"Noise-Equivalent Power", Wikipedia Encyclopedia, Retrieved: http://en.wikipedia.org/wiki/Noise-equivalent_power, (Accessed Apr. 10, 2012), 1 pg.
Richards, P L, "Bolometers for infrared and millimeter waves", Journal of Applied Physics, 76, 1 (1994); doi: 10.1063/1.357128), (1994), 25 pgs.
Su, N., et al., "Temperature Dependence of High Frequency and Noise Performance of Sb-Heterostructure Millimeter-Wave Detectors", IEEE Electron Device Letters vol. 28, No. 5, (May 2007), 336-339.

* cited by examiner

US 9,766,369 B2

DETECTOR, PREAMPLIFIER SELECTION APPARATUS, SYSTEMS, AND METHODS

RELATED APPLICATION

This application is a continuation application of U.S. application Ser. No. 13/583,118, filed on Jan. 28, 2013; which application is a U.S. National Stage Filing under 35 U.S.C. 371 from international Application No. PCT/US2010/026662, filed on 9 Mar. 2010, and published as WO 2011/112185 A1 on 15 Sep. 2011, which applications and publication are incorporated herein by reference in their entirety.

BACKGROUND

Downhole fluid samples are often captured during wireline and logging while drilling/measurement while drilling formation exploration. These samples may be used to determine various properties of formation fluid. However, during drilling operations, fluid filtrate invades the formation and tends to contaminate fluids near the well bore. To reduce the level of contamination (e.g., to where the level of fluid contamination remains at or below 5%) during sample acquisition, a considerable length of time may be spent pumping the formation. Thus, field operators are interested to know when the contamination has been reduced to an acceptable level, so that representative samples may be taken.

DETAILED DESCRIPTION

One technique that may be used to determine sampled fluid properties is that of evaluating the optical properties of the fluid sample. The optical properties of a fluid sample can in turn be used to determine the fluid's level of contamination, fluid type, fluid composition, and pressure, volume, temperature (PVT) properties. In some embodiments, the technique involves directing visible, near infra-red (IR), and mid-IR radiation through a fluid sample so that the properties of the radiation after passing through the fluid can be measured.

In many embodiments, the range of radiation wavelengths to be detected is from about 300 nm to about 5000 nm. To detect this radiation after it passes through a fluid sample, combinations of optical detectors and amplifiers (e.g., in the form of an instrumentation preamplifier) can be used. The elements of these apparatus are selected to provide an improved signal-to-noise ratio (SNR) when subjected to downhole operating conditions (e.g., a temperature range of 0 to 200 C).

Figure 1:
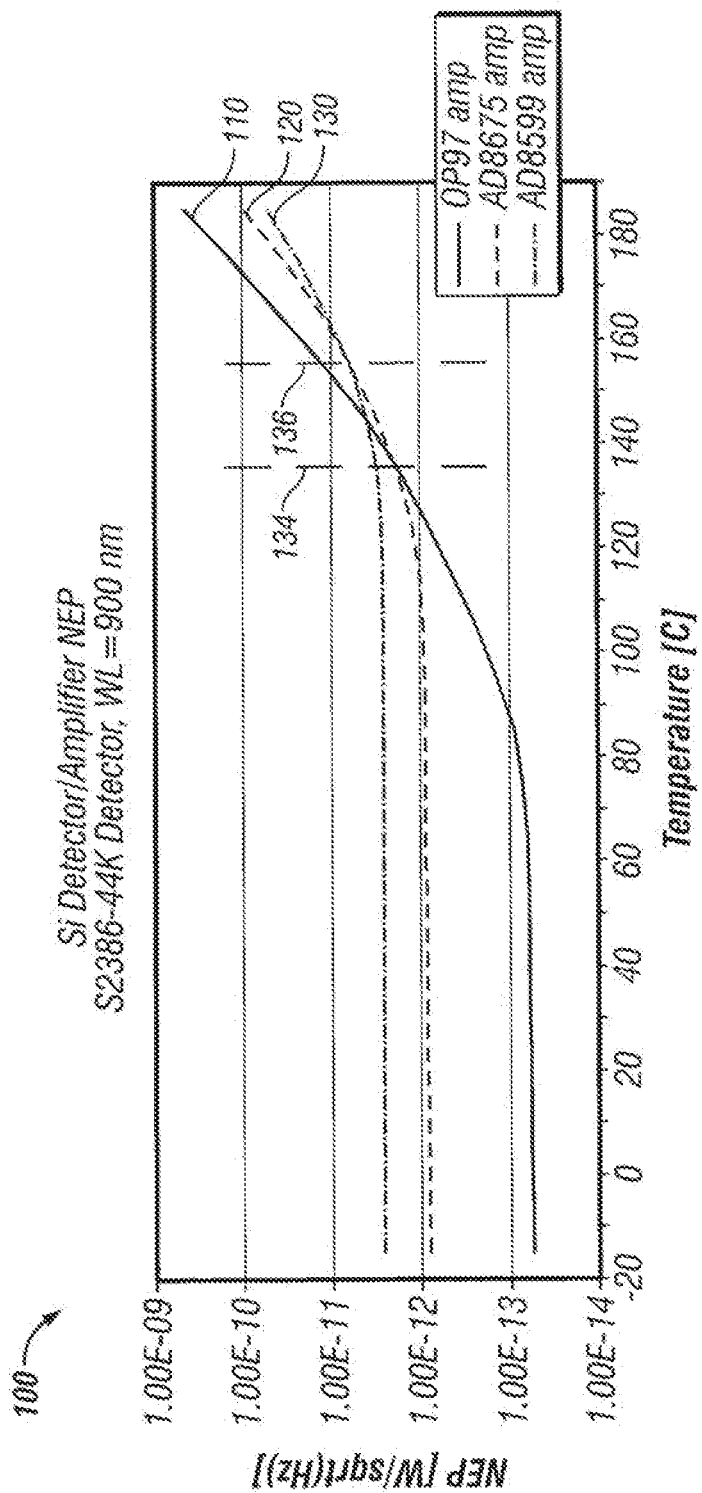
FIG. 1 is a graph illustrating the noise equivalent power characteristics of selected detector/amplifier combinations according to various embodiments of the invention.

FIG. 1 is a graph 100 illustrating the noise equivalent power (NEP) characteristics of selected detector amplifier combinations according to various embodiments of the invention. Although many different types of detector and amplifiers can be used, the combination of a single detector with multiple amplifiers has been selected in this case to clearly illustrate some basic concepts, and not as a way of limiting the potential number of embodiments. Other detector and amplifier types and specific models may thus be used.

For example, optical detector technologies that are usable in the downhole environment for various embodiments include quantum detectors (e.g., photo-diode), InGaAs detectors, thermopile detectors, and pyroelectric detectors, among others. When activated by light, these detectors produce electrical voltage or current signals, depending on the type of detector used. Signals from the detector are often processed by a selected amplifier before presentation to a data acquisition system.

The wide temperature range of downhole operations poses some challenges with respect to obtaining a usable SNR. However, by selecting an appropriate combination of an optical detector and an amplifier, these challenges can be overcome in most situations. For example, by choosing an optical detector and an amplifier that together present the lowest relative available NEP, given a particular set of environmental conditions.

Turning now to FIG. 1, it can be seen that a single S2386-44K detector is paired with three amplifiers: an OP97 amplifier, an AD8675 amplifier, and an AD8599 amplifier. The S2386-44K detector is a silicon photodiode detector available from Hamamatsu Photonics K.K. of Hamamatsu City, Japan through their U.S. office in Bridgewater, N.J. The amplifiers are all available from Analog Devices, Inc. of Norwood, Mass. in the United States of America.

The way in which the combination selected might change over temperature is readily apparent in FIG. 1, where it can be seen that the S2386-44K detector can be combined with a different one of the three amplifiers (OP97, AD8675, AD8599) to provide different levels of NEP for each combination. Thus, for temperatures less than about 136 C (see temperature crossover point 134), the OP97 amplifier provides the lowest NEP when paired with the S2386-44K detector. However, between about 136 C and 155 C, the AD8675 amplifier combined with the S2386-44K detector provides the lowest NEP. Once the temperature rises above about 155 C (see temperature crossover point 136), the AD8599 amplifier and the S2386-44K detector provide the lowest NEP combination. This is a surprising and unexpected result, one that is not apparent from viewing the manufacturer's data sheets that document the performance of individual elements.

The approach of selecting detectors and/or amplifiers recognizes, for example, that amplifiers can be selected to provide an improved SNR over an expected operating temperature range for a given detector. Thus, amplifier selection for a silicon-based detector may result in sacrificing low temperature performance, with a better high temperature SNR.

Similarly, multiple detectors may be selected to achieve an improved SNR over the entire range of wavelengths to be sensed, such as about 300 nm to about 5000 nm. In this case, a silicon-based detector (e.g., silicon photodiode) may provide the best SNR (because NEP is lower) over the 400 nm to 1000 nm range.

Likewise, the same amplifier may not be the best choice when different detectors are used. For example, a chopping amplifier like the AD8628 amplifier (from Analog Devices, Inc.) might perform better in combination with a thermopile detector, whereas the AD8599 amplifier may provide a better system SNR when used in combination with an InGaAs detector (e.g., Hamamatsu Photonics model G8421).

Individual components have specific elements that contribute to their total NEP. Thus, to determine the NEP of a particular combination of elements, several contributors to the noise power of each component can be taken into account. For example, when various noise contributors for each element in the combination of a detector and amplifier are considered over the expected downhole operating temperature range, better system performance at high temperatures may be provided by a combination that would not be chosen when operating at lower temperatures.

A circuit model can be used to calculate the NEP of a given combination, based on individual NEP element values for particular component elements (different contributing factors are often more significant than others, depending on the temperature range under consideration). Such contributing factors used in the model might include the detector shunt resistance, amplifier feedback resistance, input voltage noise of the amplifier, and input current noise of the amplifier, among others. The modeling procedure for such a combination is well known to those of ordinary skill in the art. In addition, or in the alternative, the NEP of various combinations can be experimentally determined and/or verified via measurement over the expected ranges of temperature and source wavelength.

Figure 2:
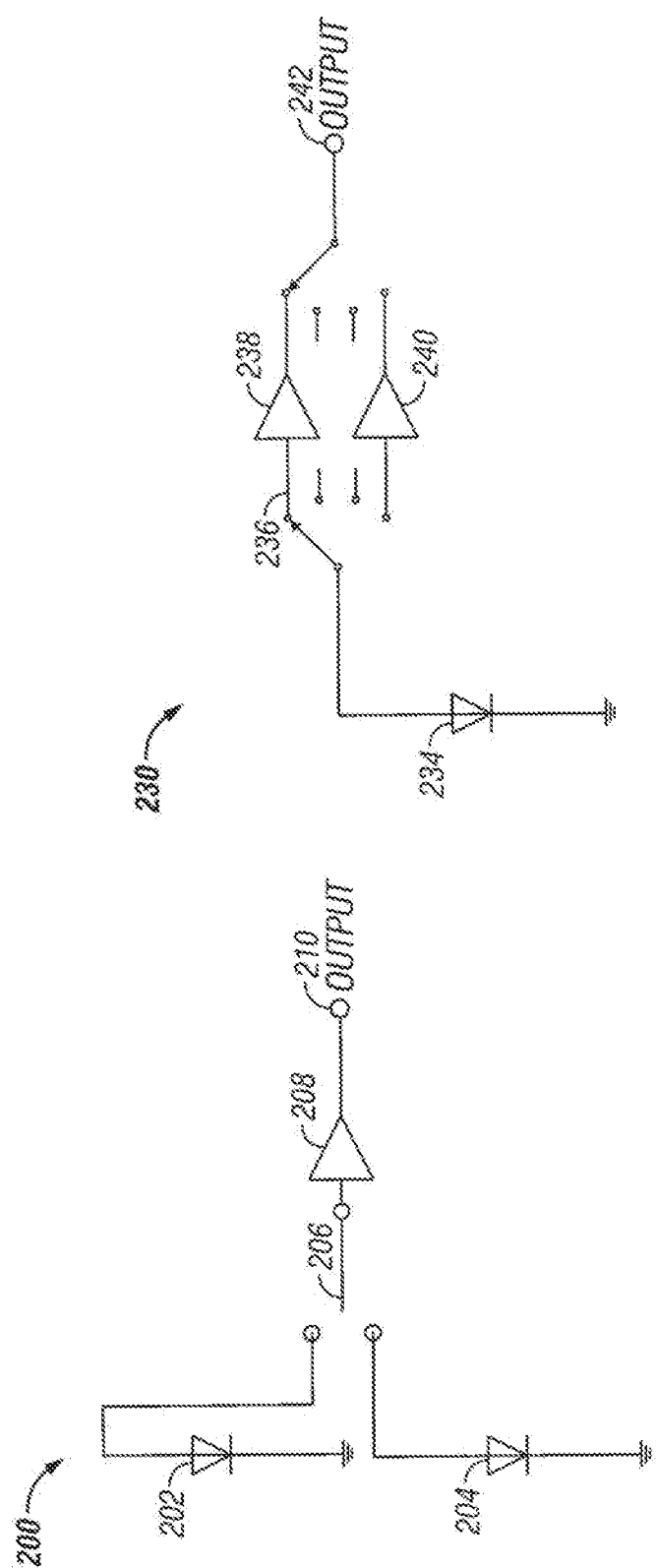
FIG. 2 illustrates schematic diagrams of optical detection apparatus, according to various embodiments of the invention.

FIG. 2 illustrates schematic diagrams of optical detection apparatus 200, 230, according to various embodiments of the invention. Here it can be seen that some embodiments are relatively simple to implement. For example, the apparatus 200 comprises an SPDT (single-pole, double-throw) switch that is used to select between two detectors 202, 204, in combination with a single amplifier 208, to provide an output signal 210. Similarly, apparatus 230 comprises an SP4T (single-pole, four-throw) switch that is used to select between two amplifiers 238, 240, in combination with a single detector 234, to provide an output signal 242. In each case, the combination of a detector and amplifier may be chosen that provides the lowest available NEP for a particular set of operating conditions, such as lower temperature versus higher temperature, lower source wavelength versus higher source wavelength, one detector type versus another detector type, and/or one amplifier make/model/type versus another amplifier make/model/type.

It should be noted that the detectors 202, 204, 234 are shown as diode detectors for simplicity, and not by way of limitation. Thermopile detectors and other types of optical detectors can also be used, as noted elsewhere in this document. Similarly, although single pole switches 206, 236 are shown, any type of switch or selector (e.g., a multiplexer) can be used to determine the operating configuration of the various apparatus described herein.

Thus, the NEP can be defined for a detector, or for a combination of a detector and amplifier. While a noise figure might be published for an amplifier, using a "low-noise" amplifier does not necessarily produce a combination of detector and amplifier that has a low NEP, given a particular set of environmental operating conditions. In several embodiments, the input noise impedance of the amplifier is substantially matched to the output impedance of the detector at the expected operating temperature. In most embodiments, the best combination is one that provides the lowest available NEP over a particular portion of the expected operating temperature range. While it can be useful to maximize performance at the highest expected operating temperature, various embodiments permit amplifiers and/or detectors to be selected for operation within selected temperature ranges, if desired.

Figure 3:
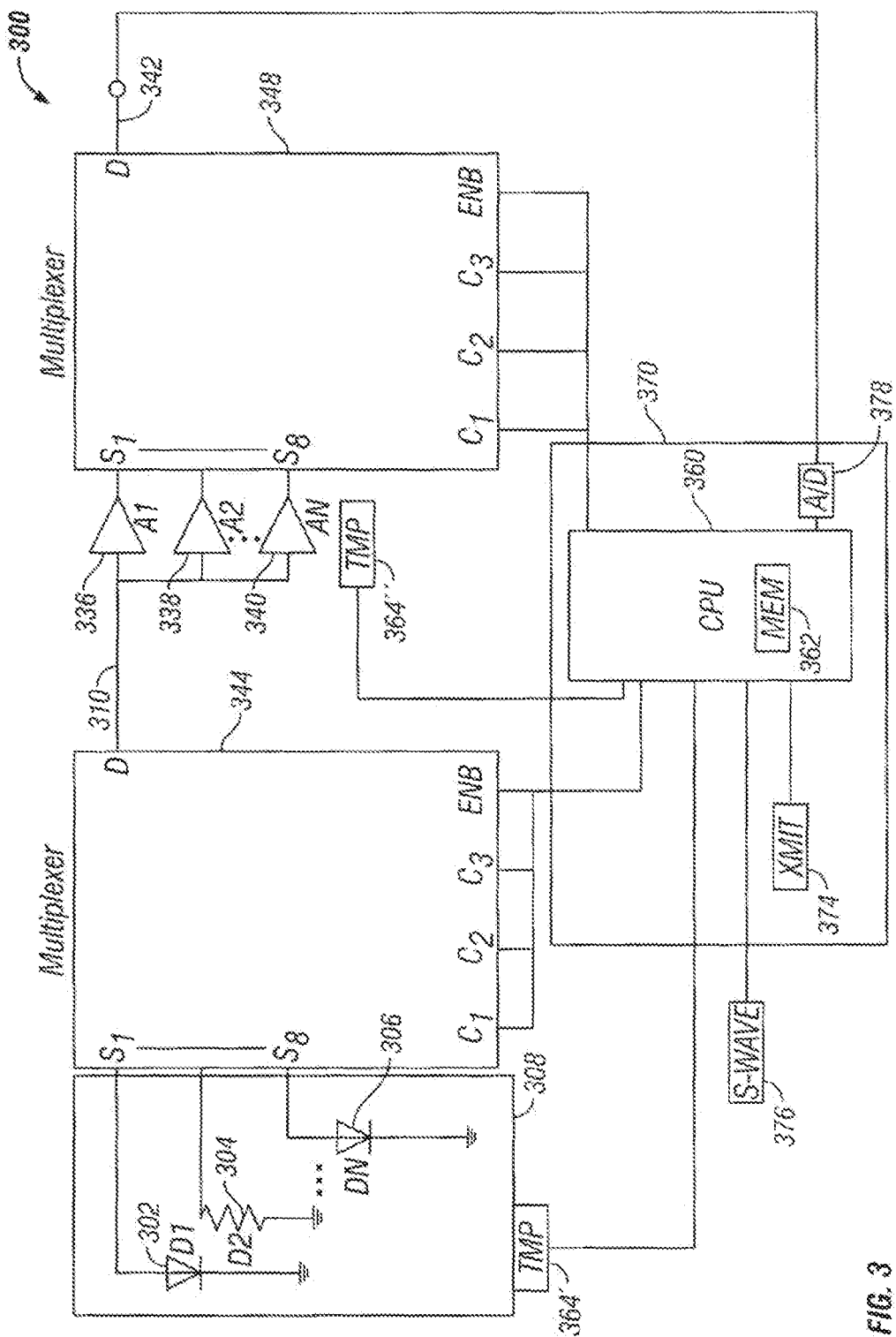
FIG. 3 is a schematic block diagram of additional optical detection apparatus, according to various embodiments of the invention.

FIG. 3 is a schematic block diagram of additional optical detection apparatus 300, according to various embodiments of the invention. Here it can be seen that multiplexers 344, 348 have been used in place of the switches 206, 236 of FIG. 2. In addition, different types of detectors 302, 304, 306 are shown, perhaps forming part of an array 308 of detectors.

The operating temperature of one or more of the detectors 302, 304, 306 can be monitored using a temperature sensor 364'. If the detectors 302, 304, 306 are proximate to each other, or mounted to the same supporting surface (e.g., as part of the array 308), such as the same substrate, this can provide a relatively simple way to monitor the operating temperature of several detectors at once.

The operating temperature of the amplifiers 336, 338, 340 can also be monitored, using a temperature sensor 364". The amplifiers 336, 338, 340 may also be mounted to a common surface (not shown in FIG. 3).

When the exposed detectors 302, 304, 306 are irradiated with an appropriate source wavelength, they produce a signal that can be selected by the multiplexer 344. This signal can be selected and passed on to one or more of the amplifiers 336, 338, 340 as detector output signal 310. Signal 310 selection may occur as a result of program instructions stored in a memory 362 coupled to a processor 360 that is electrically coupled to the multiplexer 344.

In many embodiments, the detector output signal 310 is received by at least one amplifier. Thus, as shown in FIG. 2, a single amplifier can be selected to receive the signal 310, or as shown in FIG. 3, multiple amplifiers may be used to receive the signal 310. Those of ordinary skill in the art will therefore realize after reviewing these figures and reading this disclosure that a multiplexer or other switching arrangement can be selected to provide the signal 310 to just one of the amplifiers 336, 338, 340. In this case however, the output signal 342 of the receiving amplifier is selected using the multiplexer 348. In either case, amplifier and/or signal selection may occur as a result of program instructions stored in the memory 362, and executed by the processor 360 that is electrically coupled to the multiplexers 344, 348.

The selected amplifier output signal 342 can be directed to data acquisition logic 370, where it can be digitized by an analog to digital converter 378, and stored in the memory 362. The resulting digitized amplifier output signal values may be transmitted to a surface location for further processing by a telemetry transmitter 374.

Figure 4:
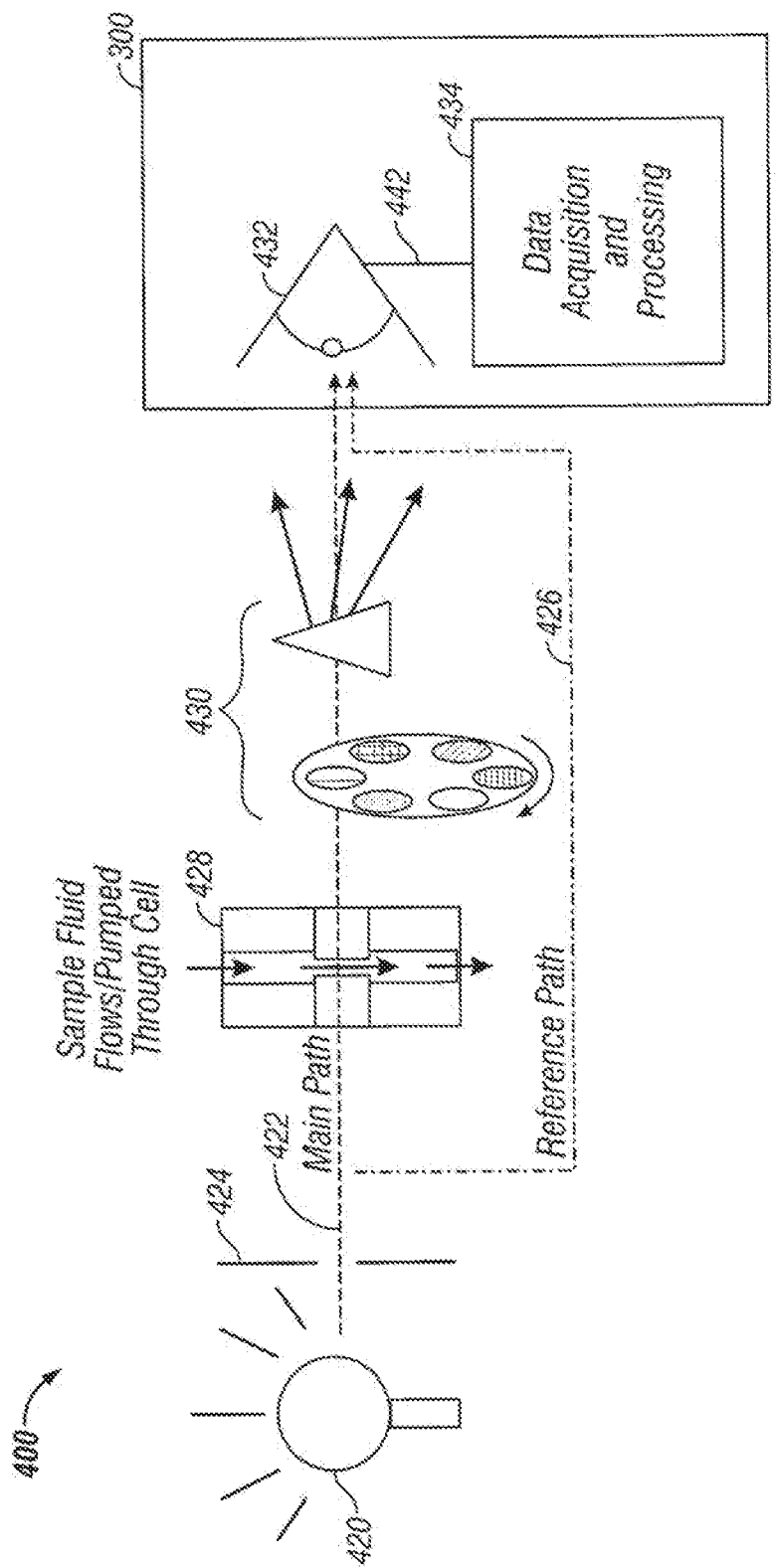
FIG. 4 is a block diagram of a more complex optical detection apparatus, including any one or more of the apparatus shown in FIGS. 2-3, according to various embodiments of the invention.

FIG. 4 is a block diagram of a more complex optical detection apparatus 400, including any one or more of the apparatus shown in FIGS. 2-3, according to various embodiments of the invention. In some embodiments, the apparatus 400 forms part of a complete spectroscopy system.

It should be noted that the apparatus 300 shown in FIG. 4 has been divided into functional entities, rather than circuit elements, as shown in FIGS. 2-3. Thus, the apparatus 300 in this case includes a detector-amplifier combination 432 (perhaps comprising detectors, amplifiers, and selection mechanisms (e.g., switches, multiplexers, etc.), as shown in FIGS. 2-3), and data acquisition and processing logic 434

(e.g., perhaps comprising data acquisition logic 370 and sensors 364, as shown in FIG. 3). The detector-amplifier combination 432 may thus comprise one or more types of detectors, including thermal detectors (e.g., pyroelectric, thermopile, etc.), and photodetectors (photoacoustic, silicon diode, PbSe, InGaAs, PMT, etc.).

The source 420 of radiation may comprise a relatively broadband source, such as one that radiates over a range of about 0.3 um to about 6 um. The source 420 may comprise a single source, or multiple sources, perhaps radiating over different wavelength bands. For example, the source 420 may comprise a tungsten filament.

A collimator 424 may be used in conjunction with the source 420 to direct the main path radiation 422 along the main path until it reaches the detector of the detector-amplifier combination 432. The collimator 424 may include a variety of optics in some embodiments, including parabolic reflectors, lenses, mirrors, etc. The collimator 424 may be used anywhere along the main radiation path 422 to improve transmission efficiency. A reference radiation path 426 may also be used in some embodiments to provide a mechanism for calibration and/or comparison.

In some embodiments, the apparatus 400 comprises a flow cell 428. In many cases, high pressure, high temperature sample fluid flows through the cell 428. The radiation from the source 420 passes through an optically transparent primary window in the cell 428, though the fluid, and then out of a secondary window. The fluid interacts with the radiation, imprinting its radiation-sensitive properties on the spectral components of the main path radiation 422.

Sapphire or other suitable materials may be used in the windows of the cell 428 to allow broadband radiation to pass through the fluid sample. Such material is usually strong enough to withstand high pressure (e.g., up to 200,000 kPa) and high temperature (e.g., up to 250 C). The gap between the primary and secondary windows can be set anywhere within a range of distances, such as between about 0.5 mm and about 3 mm. The gap may be a variable gap.

A spectral distributor 430 may be disposed to intercept the main path radiation 422. The distributor 430 may operate to separate received radiation into wavelength bands in order to determine the wavelength spectral content of the fluid being measured. The mechanism of distribution may comprise a filter array, a prism, a color wheel, or an optical grating. A rotating chopper/filter wheel may be used to modulate the radiation, while providing radiation that is periodically separated into wavelength bands.

The output signal 442 from the detector-amplifier combination 432 (e.g., similar to or identical to the output signal 342 of FIG. 3) may be conditioned, measured, and digitized by the data acquisition and processing logic 434. Digitized versions of the output signal 442 from the detector-amplifier combination 432 may then further processed into data that describes fluid properties (e.g., contamination, fluid type, GOR, composition, etc.) associated with the fluid sampled in the cell 428. This data may be stored in the logic 434 downhole, or transmitted to the surface via wireline or measurement while drilling/logging while drilling. Thus, many embodiments may be realized.

For example, referring now to FIGS. 2-4, it can be seen that an apparatus 400 may comprise a combination of a single detector and a single amplifier that have been selected to reduce the NEP among multiple available combination. The selected combination can be taken from a set of at least two detectors and one amplifier, or two amplifiers and one detector, for example. Multiple detectors and/or amplifiers can be selectively switched into operation based on minimizing the NEP of the selected detector, or a combination of the detector and amplifier.

Thus, in some embodiments, an apparatus 400 may comprise an optical detector 202, 204, 234, 302, 304, 306 and a detector amplifier 208, 238, 240, 336, 338, 340 electrically coupled to the optical detector. In most embodiments, at least one of the optical detector or the detector amplifier is to be dynamically selected via switching (e.g., using switches 206, 236 and/or multiplexers 344, 348, for example) from among at least two alternative elements to reduce the NEP of a selected detector or a combination of the selected detector and a selected amplifier to the lowest value available.

Thus, the selection to reduce available NEP can be made from among two or more detectors, or two or more amplifiers. Therefore, the alternative elements may comprise at least two (optical) detectors, or at least two (detector amplifiers.

The apparatus 400 may comprise one or more optical detector types (e.g., both thermal detectors and photo detectors). The optical detectors may be included as an array 308 of detectors.

Temperature sensors may be applied to the detector, the amplifier, or both. Thus, the apparatus 400 may comprise one or more temperature sensor 364 to sense an operating temperature of one or more optical detectors and/or one or more detector amplifiers.

A control system may be used to accomplish switching among available elements, such as additional detectors and/or amplifiers. Thus, the apparatus 400 may comprise a feedback and control system (e.g., the processor 360, coupled to the temperature sensors 364, a source wavelength sensor 376, and the multiplexers 344, 348) to monitor an operating temperature of the optical detectors, the detector amplifiers, or both, and to accomplish the switching based on the monitored operating temperature and/or the source wavelength.

In some embodiments, simple switching logic, perhaps in the form of a temperature sensor 364 and one or more switches, can be used to accomplish the switching. Thus, the apparatus 400 may comprise switching logic (e.g., individual switches 206, 236 in FIG. 2, or multiplexers 344, 348 in FIG. 3) to accomplish the switching based on an operating temperature associated with one or more of the alternative elements (i.e., optical detectors and amplifiers).

Switching logic, perhaps in the form of a wavelength sensor 376 and one or more switches, can also be used to accomplish the switching. Thus, the apparatus 400 may comprise switching logic (e.g., individual switches 206, 236 in FIG. 2, or multiplexers 344, 348 in FIG. 3) to accomplish the switching based on the wavelength of source radiation to be received by the optical detector. Thus, switching between alternative elements may be based on temperature (e.g., element operating temperature), source wavelength, or both.

The apparatus may include a source of radiation, such as a wideband or multiple narrow band sources. Thus, the apparatus 400 may comprise a wideband source 420 of radiation, or multiple narrowband sources of radiation, to be directed to the optical detector.

The apparatus 400 may include a flow cell 428. Thus, the apparatus 400 may comprise a flow cell 428 to receive a sample fluid, and to permit source radiation to pass through the sample fluid prior to being received by the optical detector.

A spectral distributor 430, such as a prism, grating, or filter wheel can be used to distribute incoming radiation to selected detectors. Thus, the apparatus 400 may comprise a spectral distributor 430 to receive source radiation, and to distribute a spectral portion of the source radiation to the optical detector.

The apparatus 400 may include data acquisition logic. Thus, the apparatus 400 may comprise data acquisition logic 370 to receive signals from the optical detector and to store values associated with the signals, and/or to transmit the values to a surface logging facility.

In some embodiments, the apparatus 400 comprises a spectroscopic analysis system. Thus, the apparatus 400 may comprise a source of optical radiation 420, and a flow cell 428 to receive fluid samples and the optical radiation, and to permit the optical radiation to pass through the fluid samples before impinging on the optical detector.

Figure 5:
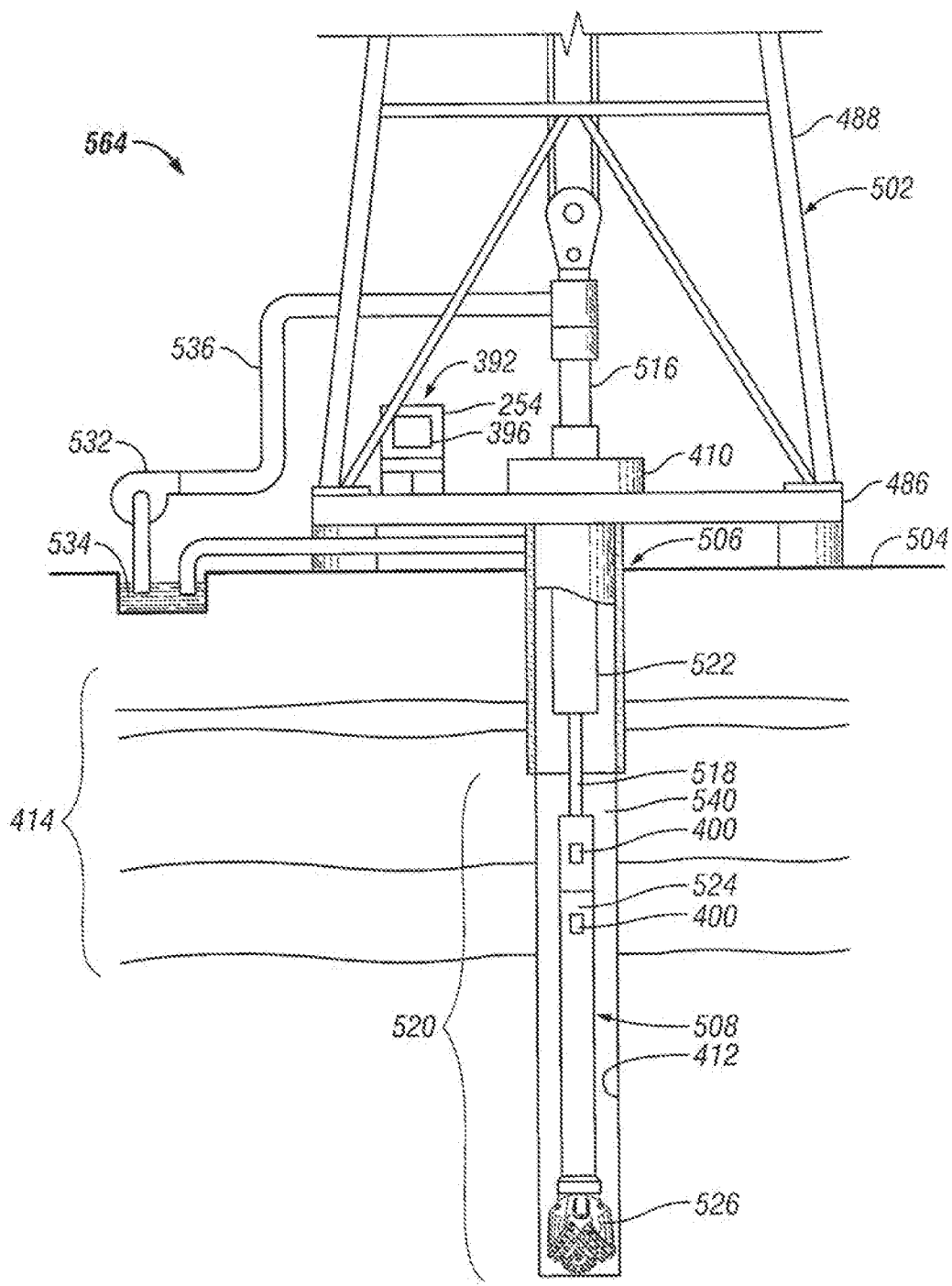
FIGS. 5-6 illustrate system embodiments of the invention.
Figure 6:
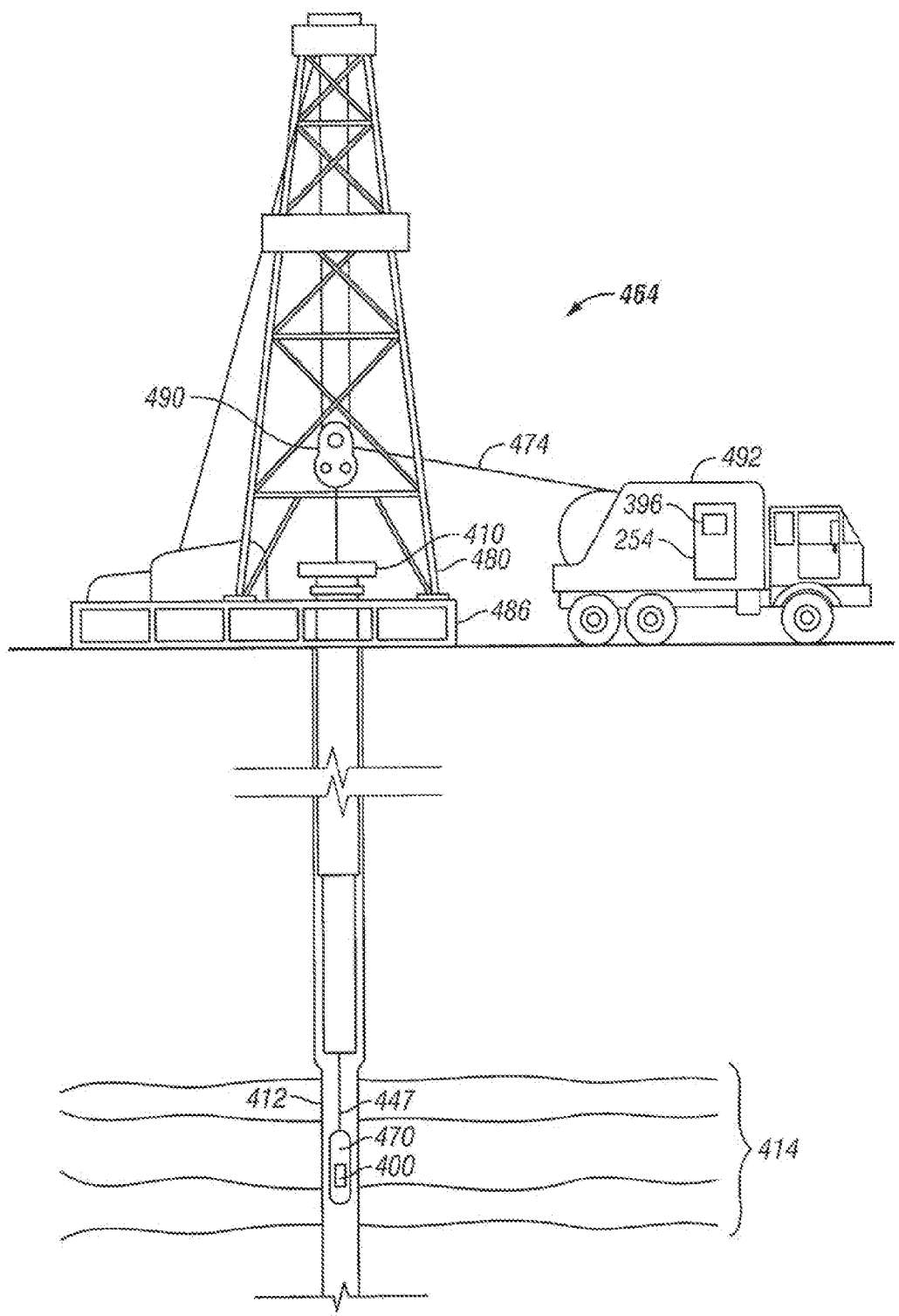

FIGS. 5-6 illustrate system embodiments of the invention. For example, FIG. 5 illustrates a drilling rig system 564 embodiment of the invention, and FIG. 6 illustrates a wireline system 464 embodiment of the invention. Thus, systems 464, 564 may comprise portions of a downhole tool, realized as a tool body 470 (e.g., as part of a wireline logging operation), or as a measurement while drilling (MWD) or logging while drilling (LWD) tool 524 as part of a downhole drilling operation.

Drilling of oil and gas wells is commonly carried out using a string of drill pipes connected together so as to form a drilling string that is lowered through a rotary table 410 into a wellbore or borehole 412. Turning now to FIG. 5, it can be seen how a system 564 may form a portion of a drilling rig 502 located at the surface 504 of a well 506. The drilling rig 502 may provide support for a drill string 508. The drill string 508 may operate to penetrate a rotary table 410 for drilling a borehole 412 through subsurface formations 414. The drill string 508 may include a Kelly 516, drill pipe 518, and a bottom hole assembly 520, perhaps located at the lower portion of the drill pipe 518. In some embodiments, one or more apparatus 400 may be carried as part of the drill string 508 or the tool 524.

The bottom hole assembly 520 may include drill collars 522, a tool 524, and a drill bit 526. The drill bit 526 may operate to create a borehole 412 by penetrating the surface 504 and subsurface formations 414. The tool 524 may comprise any of a number of different types of downhole tools including MWD (measurement while drilling) tools, LWD tools, and others.

During drilling operations, the drill string 508 (perhaps including the Kelly 516, the drill pipe 518, and the bottom hole assembly 520) may be rotated by the rotary table 410. In addition to, or alternatively, the bottom hole assembly 520 may also be rotated by a motor (e.g., a mud motor) that is located downhole. The drill collars 522 may be used to add weight to the drill bit 526. The drill collars 522 may also operate to stiffen the bottom hole assembly 520, allowing the bottom hole assembly 520 to transfer the added weight to the drill bit 526, and in turn, to assist the drill bit 526 in penetrating the surface 504 and subsurface formations 414.

During drilling operations, a mud pump 532 may pump drilling fluid (sometimes known by those of skill in the art as "drilling mud") from a mud pit 534 through a hose 536 into the drill pipe 518 and down to the drill bit 526. The drilling fluid can flow out from the drill bit 526 and be returned to the surface 504 through an annular area 540 between the drill pipe 518 and the sides of the borehole 412. The drilling fluid may then be returned to the mud pit 534, where such fluid is filtered. In some embodiments, the drilling fluid can be used to cool the drill bit 526, as well as to provide lubrication for the drill bit 526 during drilling operations. Additionally, the drilling fluid may be used to remove subsurface formation 414 cuttings created by operating the drill bit 526.

FIG. 6 shows a well during wireline logging operations. A drilling platform 486 is equipped with a derrick 480 that supports a hoist 490. Here it is assumed that the drilling string has been temporarily removed from the borehole 412 to allow a wireline logging tool body 470, such as a probe or sonde that carries a sonic tool 200, to be lowered by wireline or logging cable 474 into the borehole 412. Typically, the tool body 470 is lowered to the bottom of the region of interest and subsequently pulled upward at a substantially constant speed.

During the upward trip, the apparatus 400 included in the tool body 470 may be used to perform measurements in the borehole 412 as the body. 470 passes by. The measurement data can be communicated to a surface logging facility 392 for storage, processing, and analysis. The logging facility 392 may be provided with electronic equipment for various types of signal processing, which may be implemented by any one or more of the components of the apparatus 400 claimed as an apparatus or a system in the claims below, and/or shown in FIGS. 2-4. The log data is similar to that which may be gathered and analyzed during drilling operations (e.g., during logging while drilling operations).

The apparatus 400, which may comprise any one or more of the components previously described, may thus be located downhole. The apparatus 400, including any of the sub-components previously described, may therefore be at least partially housed by a downhole tool, perhaps taking the form of an MWD/LWD tool 524 or a tool body 470.

In some embodiments, portions of the apparatus 400, including the data acquisition and processing logic 434, may be located at the surface. Other portions of the apparatus 400 may be at least partially housed by the downhole tool. Telemetry may be used to communicate between portions of the apparatus 400 located downhole, and portions located at the surface.

The data acquisition and processing logic 434 may comprise a signal processor. The signal processor may be used to receive and digitize the output signal (e.g., provided by the apparatus 300 in FIGS. 3,4) to provide a digitized output signal.

The data acquisition and processing logic 434 may comprise a telemetry transmitter to communicate values associated with the output signal from the apparatus 200, 230 300, 400 to a surface logging facility, perhaps one that includes a signal processor. Thus, the surface logging facility and the data acquisition and processing logic 434 may be used to divide the labor employed in processing the output signal of the apparatus 400. The surface facility may comprise a display (see element 396 of FIGS. 5, 6) to display values associated with the output signal, such as a digitized version of the output signal of the apparatus 400. Thus, many embodiments may be realized.

For example, a system 464, 564 may comprise one or more apparatus 400, and a downhole tool body mechanically coupled to the apparatus 400. The system 464, 564 may comprise a measurement-while-drilling (MWD), logging-while-drilling (LWD), or wireline system. Thus, the downhole tool body can be mechanically coupled to one of an MWD, LWD, or wireline system.

The apparatus 200, 230, 300, 400; detectors 202, 204, 234, 302, 304, 306; switches 206, 236; amplifiers 208, 238, 240, 336, 338, 340, 342; signals 210, 242, 310, 442; array 308; multiplexers 344, 348; sensors 364; processor 360; memory 362; logic 370, 434; analog to digital converter 378;

logging facility 392; display 396; apparatus 400; rotary table 410; boreholes 412; formation 414; source 420; collimator 424; cell 428; spectral distributor 430; detector-amplifier combination 432; systems 464, 564; tool body 470; drilling platform 486; derrick 480; hoist 490; logging cable 474; drilling rig 502; well 506; drill string 508; Kelly 516; drill pipe 518; bottom hole assembly 520; drill collars 522; downhole tool 524; drill bit 526; mud pump 532; mud pit 534; and hose 536 may all be characterized as "modules" herein. Such modules may include hardware circuitry, and/or a processor and/or memory circuits, software program modules and objects, and/or firmware, and combinations thereof, as desired by the architect of the apparatus 400 and systems 464, 564, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for drilling operations, and thus, various embodiments are not to be so limited. The illustrations of apparatus 400 and systems 464, 564 are intended to provide a general understanding of the structure of various embodiments, and they are not intended to serve as a complete description of all the elements and features of apparatus and systems that might make use of the structures described herein.

Applications that may incorporate the novel apparatus and systems of various embodiments include a variety of electronic systems, such as televisions, cellular telephones, personal computers, workstations, radios, video players, vehicles, and location technology (e.g., GPS (Global Positioning System location technology), signal processing for geothermal tools, and smart sensor telemetry systems, among others. Some embodiments include a number of methods.

Figure 7:
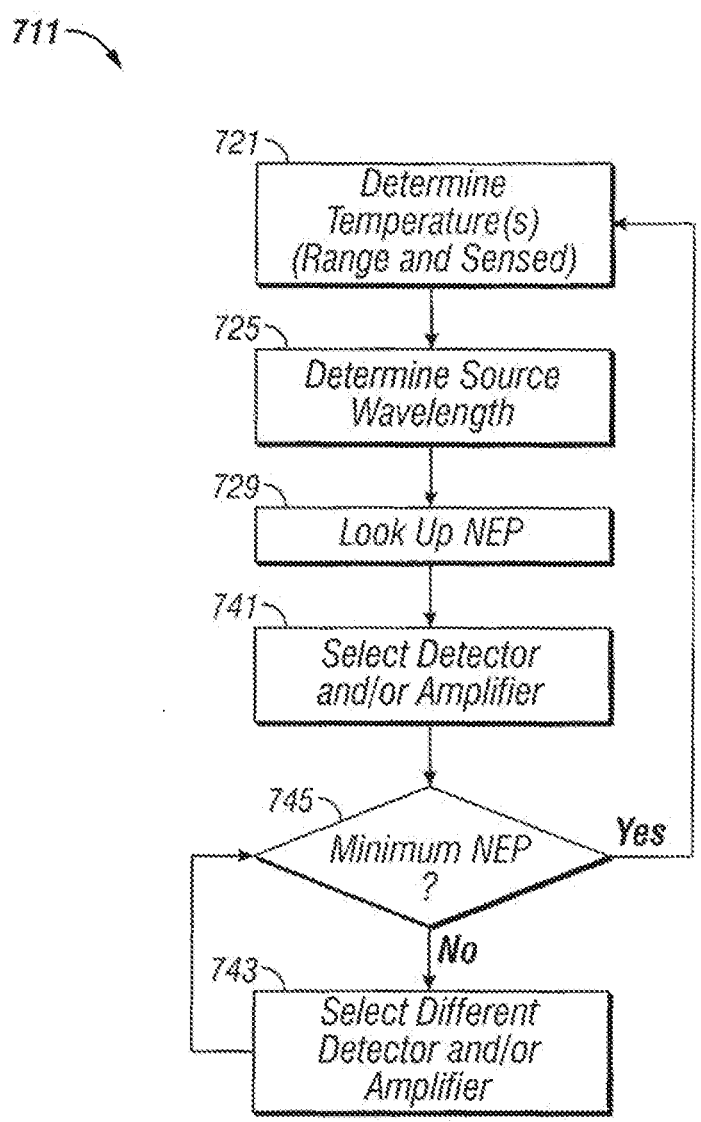
FIG. 7 is a flow chart illustrating several methods according to various embodiments of the invention.

FIG. 7 is a flow chart illustrating several methods according to various embodiments of the invention. For example, a processor-implemented method 711 to execute on one or more processors that perform methods of selecting various combinations of detectors and amplifiers to reduce NEP begin at block 721 with determining one or more temperatures, perhaps a sensed operating temperature of detectors, amplifiers, or other components in a downhole spectroscopy system, or environmental temperatures surrounding the components. A determination of whether such temperatures fall into a selected range can be made as well (e.g., the three temperature ranges shown in FIG. 1: the first, that occupies temperatures up to temperature crossover point 134, the second, which lies between temperature crossover points 134 and 136, and the third, which resides above temperature crossover point 136.

The method 711 may then continue on to block 725 with determining the wavelength of radiation emitted by the source. This can be determined by actually sensing and/or measuring the wavelength, or by accessing logic that provides an indication of the currently selected source, or sensing the state of some component that operates to adjust the wavelength emitted by the source.

The method 711 may go on to block 729 with determining a value of the NEP that can be expected, given one or more detector-amplifier combinations, perhaps using a modeling formula or a lookup table.

The method 711 may then go on to block 741 with selecting at least one of an optical detector or a detector amplifier (to couple to an optical detector) to operate as part of an optical detection system, where the selection activity is based on minimizing the NEP of the optical detector or a combination of the optical detector and the detector amplifier over a desired temperature range, or over a desired range of source wavelengths, or both. For example, the desired temperature may range from about 0 C to about 200 C. The desired source wavelength may range from about 300 nm to about 5000 nm.

The activity at block 741 may comprise selecting the detector amplifier based on an operating temperature range associated with the detector amplifier and/or the type of the optical detector, respectively. The activity at block 741 may also comprise, or comprise in the alternative, selecting an optical detector based on an operating temperature range associated with the optical detector and/or the radiation source wavelength to be received by the optical detector.

The method 711 may go on to block 745 to determine whether the minimum available NEP has been achieved. For example, the available combinations of detectors and amplifiers may be compared with a table listing combinations that should be used for a given sensed temperature and/or wavelength. If the current selected combination of a detector and amplifier coincides with that which is listed, then the minimum available NEP has been achieved. If not, then a different detector and/or amplifier can be selected at block 743 to provide a reduced NEP with respect to the currently selected combination of optical detector and amplifier.

It should be noted that the methods described herein do not have to be executed in the order described, or in any particular order. Moreover, various activities described with respect to the methods identified herein can be executed in iterative, serial, or parallel fashion. Some activities may be added, and some of the included activities may be left out. Information, including parameters, commands, operands, and other data, can be sent and received in the form of one or more carrier waves.

Figure 8:
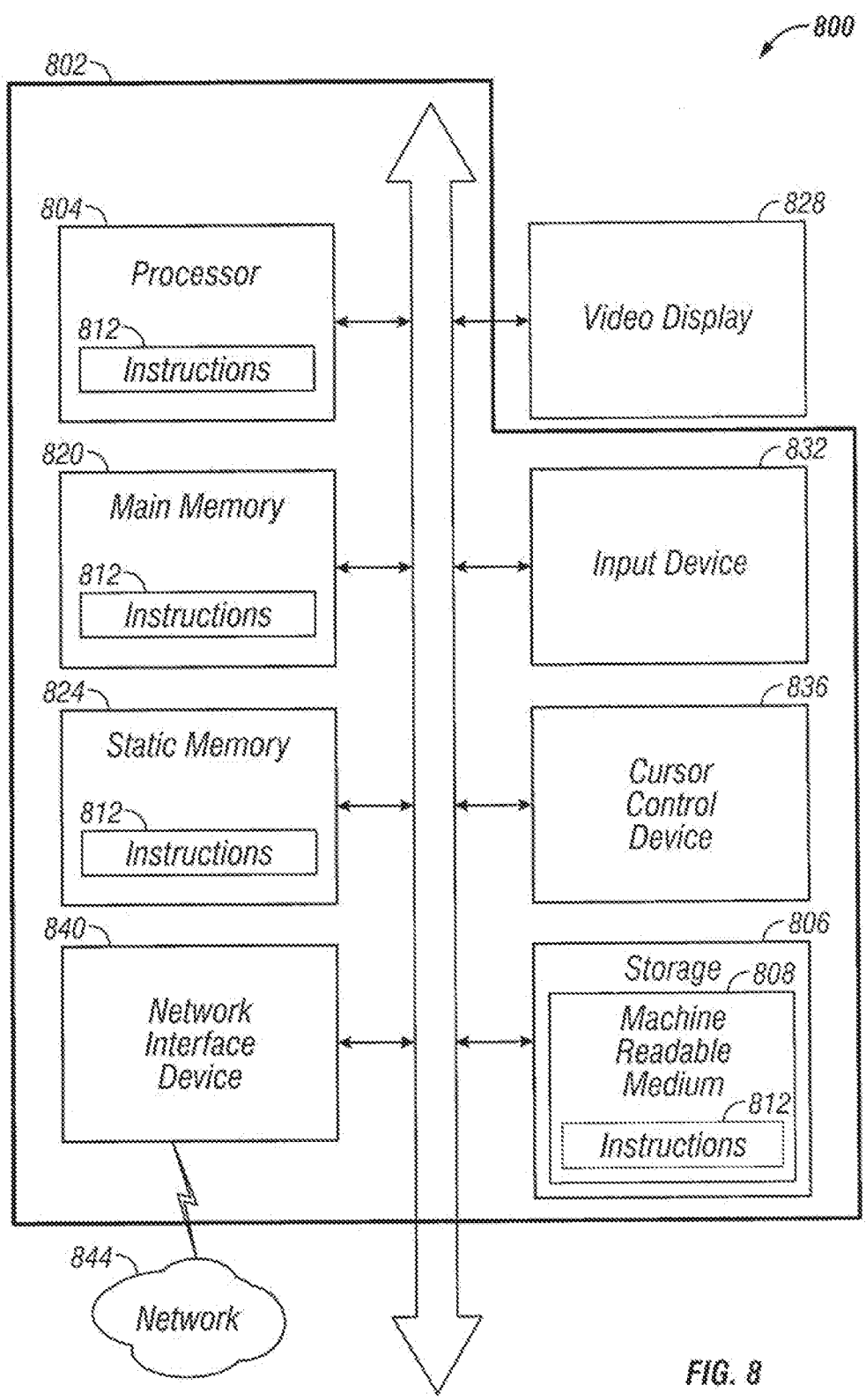
FIG. 8 is a block diagram of an article according to various embodiments of the invention.

FIG. 8 is a block diagram of an article 800 of manufacture, including a specific machine 802, according to various embodiments of the invention. Upon reading and comprehending the content of this disclosure, one of ordinary skill in the art will understand the manner in which a software program can be launched from a computer-readable medium in a computer-based system to execute the functions defined in the software program.

One of ordinary skill in the art will further understand the various programming languages that may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those of ordinary skill in the art, such as application program interfaces or interprocess communication techniques, including remote procedure calls. The teachings of various embodiments are not limited to any particular programming language or environment. Thus, other embodiments may be realized.

For, example, an article 800 of manufacture, such as a computer, a memory system, a magnetic or optical disk, some other storage device, and/or any type of electronic device or system may include one or more processors 804 coupled to a machine-readable medium 808 such as a memory (e.g., removable storage media, as well as any memory including an electrical, optical, or electromagnetic conductor comprising tangible media) having instructions 812 stored thereon (e.g., computer program instructions), which when executed by the one or more processors 804 result in the machine 802 performing any of the actions described with respect to the methods above.

The machine 802 may take the form of a specific computer system having a processor 804 coupled to a number of components directly, and/or using a bus 816. Thus, the machine 802 may be similar to or identical to the workstation 392 shown in FIGS. 5 and 6, or the data acquisition and processing logic 434 in the apparatus 400 of FIG. 4.

Turning now to FIG. 8, it can be seen that the components of the machine 802 may include main memory 820, static or non-volatile memory 824, and mass storage 806. Other components coupled to the processor 804 may include an input device 832, such as a keyboard, or a cursor control device 836, such as a mouse. An output device 828, such as a video display, may be located apart from the machine 802 (as shown), or made as an integral part of the machine 802.

A network interface device 840 to couple the processor 804 and other components to a network 844 may also be coupled to the bus 816. The instructions 812 may be transmitted or received over the network 844 via the network interlace device 840 utilizing any one of a number of well-known transfer protocols (e.g., HyperText Transfer Protocol). Any of these elements coupled to the bus 816 may be absent, present singly, or present in plural numbers, depending on the specific embodiment to be realized.

The processor 804, the memories 820, 824, and the storage device 806 may each include instructions 812 which, when executed, cause the machine 802 to perform any one or more of the methods described herein. In some embodiments, the machine 802 operates as a standalone device or may be connected (e.g., networked) to other machines. In a networked environment, the machine 802 may operate in the capacity of a server or a client machine in server-client network environment, or as a peer machine in a peer-to-peer (or distributed) network environment.

The machine 802 may comprise a personal computer (PC), a workstation, a tablet PC, a set-top box (STB), a PDA, a cellular telephone, a web appliance, a network router, switch or bridge, server, client, or any specific machine capable of executing a set of instructions (sequential or otherwise) that direct actions to be taken by that machine to implement the methods and functions described herein. Further, while only a single machine 802 is illustrated, the term "machine" shall also be taken to include any collection of machines that individually or jointly execute a set (or multiple sets) of instructions to perform any one or more of the methodologies discussed herein.

While the machine-readable medium 808 is shown as a single medium, the term "machine-readable medium" should be taken to include a single medium or multiple media (e.g., a centralized or distributed database, and/or associated caches and servers, and or a variety of storage media, such as the registers of the processor 804, memories 820, 824, and the storage device 806 that store the one or more sets of instructions 812. The term "machine-readable medium" shall also be taken to include any medium that is capable of storing, encoding or carrying a set of instructions for execution by the machine and that cause the machine 802 to perform any one or more of the methodologies of the present invention, or that is capable of storing, encoding or carrying data structures utilized by or associated with such a set of instructions. The terms "machine-readable medium" or "computer-readable medium" shall accordingly be taken to include tangible media, such as solid-state memories and optical and magnetic media.

Various embodiments may be implemented as a standalone application (e.g., without any network capabilities), a client-server application or a peer-to-peer (or distributed) application. Embodiments may also, for example, be deployed by Software-as-a-Service (SaaS), an Application Service Provider (ASP), or utility computing providers, in addition to being sold or licensed via traditional channels.

Using the apparatus, systems, and methods disclosed, those employed in the petroleum recovery industry and other industries may now be able to more accurately assess the composition of fluid samples while accommodating a wide range of operating temperatures and spectroscopic radiation source wavelengths. Increased operational efficiency and client satisfaction may result.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description and the figures, with each claim standing on its own as a separate embodiment.

What is claimed is:

1. An apparatus comprising:
a set of optical detectors and a set of detector amplifiers;

a switch circuitry coupled to the set of optical detectors and to the set of detector amplifiers;

a set of sensors that includes a temperature sensor to sense an operating temperature of at least one optical detector of the set of optical detectors or at least one detector amplifier of the set of detector amplifiers; and a processor coupled to the set of sensors and to the switch circuitry, the processor operable to control the switch circuitry to select an optical detector-detector amplifier pair from the set of optical detectors and the set of detector amplifiers based on:

output received by the processor from the set of sensors that the selected optical detector has a minimum noise equivalent power (NEP) of the optical detectors of the set of optical detectors or the selected optical detector-detector amplifier pair has a minimum noise equivalent power (NEP) of optical detector-detector amplifier pairs from the set of optical detectors and the set of detector amplifiers; and the operating temperature being within an operating temperature range.

2. The apparatus of claim 1, wherein the set of optical detectors includes at least two optical detectors and the set of detector amplifiers includes at least two detector amplifiers.

3. The apparatus of claim 1, wherein the set of sensors includes a wavelength sensor.

4. The apparatus of claim 1, wherein the switch circuitry includes a multiplexer.

5. The apparatus of claim 1, wherein the switch circuitry includes two multiplexers, one multiplexer having inputs to receive signals from the set of optical detectors and having an output to provide an input signal to the set of detector amplifiers, and the other multiplexer having inputs to receive output signals from the set of detector amplifiers and having an output to provide an output signal.

6. The apparatus of claim 5, wherein the output of the multiplexer having inputs to receive output signals from the set of detector amplifiers is coupled to the processor via an analog to digital converter.

7. The apparatus of claim 1, further comprising a spectral distributor to receive source radiation and to distribute a spectral portion of the source radiation to the optical detector of the selected optical detector-detector amplifier pair.

8. The apparatus of claim 1, wherein the set of sensors includes a source wavelength sensor arranged with the processor to control the switch circuitry to select an optical detector-detector amplifier pair based on output from the source wavelength sensor.

9. The apparatus of claim 1, wherein the set of detector amplifiers comprises one or more thermal detectors and/or one or more photodetectors.

10. A system comprising:
a sample cell;
an apparatus arranged to receive optical radiation from the sample cell at an optical detector of a set of optical detectors of the apparatus, the apparatus including:
a set of detector amplifiers;
a switch circuitry coupled to the set of optical detectors and to the set of detector amplifiers;
a set of sensors that includes a temperature sensor to sense an operating temperature of at least one optical detector of the set of optical detectors or at least one detector amplifier of the set of detector amplifiers; and
a processor coupled to the set of sensors and to the switch circuitry, the processor operable to control the switch circuitry to select the optical detector as part of an optical detector-detector amplifier pair from the set of optical detectors and the set of detector amplifiers based on:

output received by the processor from the set of sensors that the selected optical detector has a minimum noise equivalent power (NEP) of the optical detectors of the set of optical detectors or the selected optical detector-detector amplifier pair has a minimum noise equivalent power (NEP) of optical detector-detector amplifier pairs from the set of optical detectors and the set of detector amplifiers; and the operating temperature being within an operating temperature range; and data acquisition and processing logic arranged to receive an output signal from the selected optical detector-detector amplifier pair.

11. The system of claim 10, further comprising a wideband source of radiation or multiple narrowband sources of radiation arranged to irradiate the sample cell to generate the optical radiation received by the apparatus.

12. The system of claim 10, wherein the sample cell and the apparatus are arranged in a downhole tool body mechanically coupled to at least one of a measurement-while-drilling, a logging-while-drilling, and a wireline system.

13. The system of claim 10, wherein the sample cell is structured to receive a sample fluid and to permit source radiation to pass through the sample fluid prior to being received by the apparatus.

14. The system of claim 10, further comprising a spectral distributor disposed between the sample cell and the apparatus.

15. A method comprising:
selecting an optical detector-detector amplifier pair from a set of optical detectors and a set of detector amplifiers, via a switch circuitry, based on output received by a processor from a set of sensors operatively coupled to the processor, and based on the selected optical detector having a minimum noise equivalent power (NEP) of the optical detectors of the set of optical detectors or the selected optical detector-detector amplifier pair having a minimum noise equivalent power (NEP) of optical detector-detector amplifier pairs from the set of optical detectors and the set of detector amplifiers, wherein selecting the optical detector-detector amplifier pair includes selecting the detector amplifier based on an operating temperature range associated with at least one optical detector of the set of optical detectors or at least one the detector amplifier of the set of detector amplifiers.

16. The method of claim 15, wherein selecting the optical detector-detector amplifier pair includes selecting the optical detector based on an operating temperature range associated with the optical detector and/or a radiation source wavelength associated with operation of the optical detector.

17. The method of claim 15, wherein the method includes generating optical radiation from a source, directed to a sample cell, disposed in a borehole, from which resultant optical radiation impinges on the selected optical detector.

* * * * *